United States Patent [19]

Shimizu et al.

[11] Patent Number: 4,982,007

[45] Date of Patent: Jan. 1, 1991

[54] PROCESS FOR SELECTIVELY HYDROFORMULATING DIOLEFIN

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 489,837

[22] Filed: Mar. 2, 1990

Related U.S. Application Data

[62] Division of Ser. No. 275,082, filed as PCT JP88/00263 on Mar. 12, 1988, published as WO88/07033 on Sep. 22, 1988, abandoned.

[30] Foreign Application Priority Data

Mar. 12, 1987 [JP] Japan .................................. 62-57098

[51] Int. Cl.$^5$ ............................................. C07C 45/50
[52] U.S. Cl. ........................................ 568/429; 568/428; 568/454
[58] Field of Search ................. 568/428, 429, 454, 451

[56] References Cited

U.S. PATENT DOCUMENTS

| | | | |
|---|---|---|---|
| 4,113,781 | 9/1978 | Aquila et al. | 568/429 |
| 4,268,688 | 5/1981 | Tinker et al. | 568/429 |
| 4,435,585 | 3/1984 | Crameria et al. | 568/429 |
| 4,694,100 | 9/1987 | Shimizu et al. | 568/429 |

FOREIGN PATENT DOCUMENTS

| | | | |
|---|---|---|---|
| 0282066 | 9/1988 | European Pat. Off. | 560/105 |
| 0304495 | 3/1989 | European Pat. Off. | 560/105 |
| 63233945 | 9/1989 | European Pat. Off. | 560/105 |
| 2235466 | 4/1974 | Fed. Rep. of Germany | 568/429 |
| 58-210033 | 12/1983 | Japan | 568/445 |
| 59-110643 | 7/1984 | Japan | 568/445 |

*Primary Examiner*—Werren B. Lone
*Attorney, Agent, or Firm*—Scully, Scott, Murphy & Presser

[57] ABSTRACT

A process for selectively hydroformylating a diolefin, which comprises reacting a (1-arylethyl)vinylbenzene with carbon monoxide and hydrogen under the conditions of 40° to 200° C. in reaction temperature and 5 kg/cm$^2$ or above in reaction pressure in the presence of a transition metal carbonylation catalyst to thereby selectively hydroformylating only the vinyl group and produce α-((1-arylethenyl)phenyl)propionaldehyde. The starting material to be hydroformylated may be a mixture of the (1-arylethenyl)vinylbenzene with a 1,1-di(substituted aryl)ethylene not substituted by a vinyl group.

15 Claims, No Drawings

PROCESS FOR SELECTIVELY HYDROFORMULATING DIOLEFIN

This application is a continuation, of application Ser. No. 275,082, filed as PCT JP88/00263 on Mar. 12, 1988, published as WO88/07033 on Sep. 22, 1988 abandoned.

TECHNICAL FIELD

This invention relates to a process for selectively hydroformylating diolefin. More particularly, the invention relates to a process for producing unsaturated aldehyde by selectively carbonylating diolefin.

Furthermore, the invention relates to a process for selectively hydroformylating diolefin which is contaminated with certain monoolefins.

BACKGROUND ART

The method of hydroformylation to prepare aldehyde by reacting olefin with carbon monoxide and hydrogen are employed widely in industry, for example, in connection with monoolefins.

However, with regard to diolefins, such instance is few. For example, in Japanese Laid-Open Patent Publication Nos. 58-210033 and 59-110643, 5-ethylidene bicyclo[2.2.1]heptene-2 having two carbon-carbon double bonds is reacted, however, it is disclosed that formyl groups are introduced into the two unsaturated groups of the compound. In the same references, a formyl group is introduced into one of the unsaturated groups by regulating the amount of hydrogen and carbon monoxide to be used.

The inventors of the present application have found out that, with regard to specific diolefins, a formyl group is introduced into only one of the unsaturated groups under specific conditions, thereby accomplishing the present invention.

DISCLOSURE OF INVENTION

That is, the present invention relates to a process for selective hydroformylation which is characterized in that (1-arylethenyl)vinylbenzene represented by the following formula (I) is reacted with hydrogen and carbon monoxide at a reaction temperature of 40°–200° C. and a reaction pressure of 5 kg/cm² in the presence of a transition metal complex carbonylation catalyst to prepare α-((1-arylethenyl)phenyl)-propionaldehyde represented by the following formula (II).

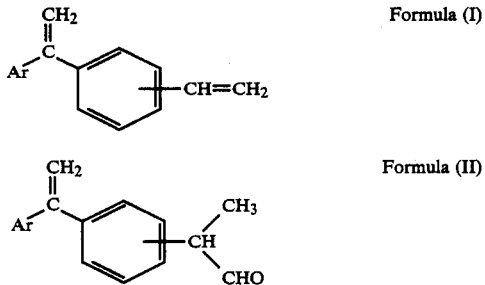

(wherein Ar is an aryl group which can have a substituent group except vinyl group)

The present invention is described in more detail in the following.

The aryl group Ar in the above (1-arylethenyl)-vinylbenzene is exemplified by aryl groups such as phenyl, alkylphenyl, alkoxyphenyl, phenoxyphenyl and biphenyl groups as well as aryl groups in which various other substituent groups except vinyl group are introduced to phenyl groups. As such substituent group, carboxyl group, hydroxyl group, alkoxy group and alkoxycarbonyl group are exemplified.

More particularly, the above (1-arylethenyl)vinylbenzenes are exemplified (1-phenylethenyl)vinylbenzene, (1-tolylethenyl)vinylbenzene, (1-xylylethenyl)vinylbenzene, and (1-ethylphenylethenyl)vinylbenzene, having phenyl, tolyl or xylyl as the aryl group as well as (1-hydroxyphenylethenyl)vinylbenzene, (1-methoxyphenylethenyl)vinylbenzene, (1-dimethoxyphenylethenyl)vinylbenzene, (1-ethoxyphenylethenyl)vinylbenzene, (1-carboxyphenylethenyl)vinylbenzene, (1-methoxycarbonylphenylethenyl)vinylbenzene, (1-di(-methoxycarbonyl)phenylethenyl)vinylbenzene and (1-ethoxycarbonylphenylethenyl)vinylbenzene.

In the above compounds, all position isomers in view of the positions of substituent groups are included, however, m-isomers are preferable.

According to the method of the present invention, the compound of the formula (II) is produced by selectively hydroformylating the vinyl group. In the case that the aryl group Ar in the compound of the foregoing formula (I) is an alkyl group or the like, the selective hydroformylation cannot be attained because all the double bonds are hydroformylated under the said condition.

By the hydroformylation according to the present invention, only the vinyl group is hydroformylated selectively in the compound of the foregoing formula (I) and the ethenyl group having the aryl groups does not react substantially in the reaction.

Accordingly, the compounds produced by the reaction of the present invention are those in which a formyl group and a hydrogen atom are added to the vinyl group of the compound of the foregoing formula (I).

Especially, the position of the addition of formyl group is generally the α-position in the vinyl group.

Therefore, the compounds of α-((1-arylethenyl)-phenyl)propionaldehydes of the formula (II) that are produced by the method of the present invention in correspondence with the foregoing compounds of the formula (I) are, for example, α-((1-phenylethenyl)-phenyl)propionaldehyde, α-((1-tolylethenyl)phenyl)-propionaldehyde, α-((1-xylylethenyl)phenyl)propionaldehyde, α-((1-ethylphenylethenyl)phenyl)propionaldehyde, α-((1-hydroxyphenylethenyl)phenyl)propionaldehyde, α-((1-methoxyphenylethenyl)phenyl)propionaldehyde, α-((1-dimethoxyphenylethenyl)phenyl)propionaldehyde, α-((1-ethoxyphenylethenyl)phenyl)propionaldehyde, α-((1-carboxyphenylethenyl)phenyl)propionaldehyde, α-((1-methoxycarbonylphenylethenyl)phenyl)propionaldehyde, α-((1-di(methoxycarbonyl)phenylethenyl)phenyl)propionaldehyde and α-((1-ethoxycarbonylphenylethenyl)phenyl)propionaldehyde.

In the following, the conditions for hydroformylation will be described.

The complex catalysts to be used are complexes of transition metals such as Ni, Co, Fe, Mo, Pt, Rh, Ir, Ru and Re, and preferably, the complexes of precious metals such as Pt, Rh, Ir and Ru. As the transition metals, those having oxidation numbers from 0 to the highest number can be used. Usable complexes are those having ligands of halogen atoms, trivalent phosphorus compounds, π-allyl group, amines, nitriles, oximes, olefins, hydrogen or carbon monoxide.

The transition metal complex catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclodecatriene dichlorocomplex, bistriphenylphosphine dicarbonyl complex, bistriphenylphosphine acetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine complex, bischlorotetracarbonyl complex and dicarbonyl acetylacetonate complex.

Furthermore, the compounds which can produce the above metal complexes in the reaction system can also be used by introducing them into the reaction system. That is, phosphine, nitrile, allyl compound, amine, oxime, olefin or carbon monoxide which is able to be the ligands to the oxides, sulfates or chlorides of the above transition metals, are simultaneously added into the reaction system.

The above phosphines to be ligand is exemplified by triphenylphosphine, tritolylphosphine, tributylphosphine, tricyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclodecatriene.

The use quantity of a complex catalyst or a compound which can produce a complex is 0.0001 to 0.5 mole, preferably 0.001 to 0.1 mole to one mole of (1-arylethenyl)-vinylbenzene (formula I). When the compound which produces a complex is used, the addition quantity of the compound to form ligands is 0.8 to 10 moles, preferably 1 to 4 moles, to one mole of the compound to produce a complex.

Furthermore, in order to accelerate the rate of reaction, it is possible to add inorganic halides such as hydrogen chloride or boron trifluoride, or organic iodide such as methyl iodide.

When these halides are added, the quantities of them are 0.1 to 30 times by mole, preferably 1 to 15 times by mole, as halogen atoms to 1 mole of the complex catalyst or the compound to produce a complex. Even though it depends upon the kind of catalyst, if the addition quantity is less than 0.1 mole, the effect of the addition cannot be expected sometimes. If the addition quantity exceeds 30 times by moles, the catalytic activity is lowered to the contrary and halogen atoms are added to the double bonds of (1-arylethenyl)vinylbenzene (formula I) which fact is a bar to the aimed reaction.

The carbonylation is carried out at 40° to 200° C., preferably 50° to 150° C., in reaction temperature. If the reaction temperature is below 40° C., the rate of reaction is very low which is not acceptable in practice. On the other hand, if the temperature of carbonylation is above 200° C., it is not desirable because the vinyl group is carbonylated and the carbon-carbon double bond (ethylidene group) of internal olefin-type is also carbonylated to reduce the selectivity, in addition, side reactions such as polymerization and hydrogen addition and decomposition of complex catalyst are caused to occur.

If the reaction pressure is 5 kg/cm$^2$ or above, it can be selected arbitrary. When the reaction pressure is lower than 5 kg/cm$^2$, the rate of reaction is very low, which cannot be adopted practically. When the reaction pressure is higher, it is desirable because the reaction proceeds faster. However, a too high pressure necessitates a very high pressure resistance for a reaction vessel, so that there is naturally a limit in view of the designing of reaction equipment.

Furthermore, the possibility that the vinyl group is carbonylated and the carbon-carbon double bond (ethylidene group) of internal olefin-type is also carbonylated, is increased. Accordingly, the pressure of not higher than 500 kg/cm$^2$ is practically sufficient.

The reaction is continued until the lowering of pressure owing to the absorption of the mixed gas of carbon monoxide and hydrogen, is not observed. The reaction time of 4 to 20 hours is generally sufficient.

The carbon monoxide and hydrogen that are necessary for the reaction can be fed either separately or by mixing them previously. The molar ratio of carbon monoxide and hydrogen to be fed into the reaction system can be selected arbitrary. In this carbonylation, carbon monoxide and hydrogen are consumed or absorbed accurately at a molar ratio of 1:1. Accordingly, because a component which is supplied in excess remains unreacted, the reaction can be proceeded again when the other component is supplied at the time when the lowering of pressure is ceased. Even though it depends upon the size of reaction vessel and the mode of reaction, it is generally most effective that carbon monoxide and hydrogen are fed in a molar ratio of 1:1.

In the hydroformylation of the present invention, it is possible to use solvents which are inert to the carbonylation, for the purpose of the removal of heat. The solvents which are inert to carbonylation are exemplified by polar solvents such as ethers, ketones and alcohols, and non-polar solvents such as parafins, cycloparafins and aromatic hydrocarbons. However, desirable results can be obtained generally without any solvent.

After the hydroformylation, the reaction product is subjected to separation, preferably by distillation under reduced pressure and the aimed product of α-((1-arylethenyl)phenyl)propionaldehyde (formula II) and catalyst can be separated quite easily. The recovered complex catalyst can be used again for the next carbonylation process.

In the present invention, (1-arylethenyl)-vinylbenzene of the foregoing formula (I) as the starting material can be the one which is contaminated with 1,1-di(substituted aryl)ethylene which is represented by the following formula (III).

(in which Ar$_1$, Ar$_2$ are the same or different substituted aryl groups and their substituent groups can be replaced by those other than vinyl group.)

That is, it was found out by the present inventors that 1,1-di(substituted aryl)ethylene of the above formula (III) is not hydroformylated substantially under the conditions to hydroformylate the vinyl group of (1-arylethenyl)vinylbenzene of the formula (I) of the present invention.

Accordingly, the material used for the hydroformylation of the present invention can be a mixture containing 1,1-di(substituted aryl)ethylene of the above formula (III).

In 1,1-di(substituted aryl)ethylene of the above formula (III), two substituted aryl groups are connected to the same carbon atom of the ethylene moiety.

The substituted aryl group herein referred to means an aromatic group which may have a substituent group or groups other than vinyl group. It is exemplified by phenyl group and naphthyl group having no substituent group as well as aryl groups having alkyl group, alkoxy groups, aryloxy groups or the like.

Such 1,1-di(substituted aryl)ethylenes are exemplified by 1,1-diphenylethylene having no substituent group, and substituted 1,1-diphenylethylenes in which the substituted aryl groups are alkylphenyls such as methylphenyl, dimethylphenyl, ethylphenyl, methylethylphenyl, propylphenyl, diethylphenyl and butylphenyl; alkoxyphenyl groups in which the substituted aryl groups are such as methoxyphenyl, dimethoxyphenyl, ethoxyphenyl, propoxyphenyl and butoxyphenyl; non-condensed polycyclic aryl groups such as phenylphenyl group, phenoxyphenyl group and benzoylphenyl group; condensed polycyclic aryl groups of alkylnaphthyl groups such as methylnaphthyl, dimethylnaphthyl and ethylnaphthyl and alkoxynaphthyl groups such as methoxynaphthyl, dimethoxynaphthyl and ethoxynaphthyl.

As described in the foregoing passages, the mixture of (1-arylethenyl)vinylbenzene of the foregoing formula (I) and 1,1-di(substituted aryl)ethylene of the foregoing formula (III) can be used as the starting material used for the hydroformylation in the present invention.

In an embodiment of the invention to use a preferable material as a mixture, 1-phenyl-1-ethylphenylethane is dehydrogenated and the dehydrogenation product from this dehydrogenation step is hydroformylated.

That is, this method consists of the following dehydrogenation step (I) and hydroformylation step (II).

Step (I): In this process, 1-phenyl-1-ethylphenylethane is brought into contact with iron oxide and/or chromium oxide dehydrogenation catalyst at a temperature of 400° to 650° C. in the presence of an inert gas to obtain a dehydrogenation product containing at least 1-phenyl-1-ethylphenyl-ethylene represented by the formula (B) and 1-phenyl-1-vinylphenyl-ethylene represented by the formula (C), and Step (II): the dehydrogenation product containing at least 1-phenyl-1-ethylphenyl-ethylene represented by the formula (B) and 1-phenyl-1-vinylphenyl-ethylene represented by the formula (C) obtained in Step (I) is hydroformylated with carbon monoxide and hydrogen in the presence of a transition metal carbonylation catalyst at 40°–200° C. in reaction temperature and 5 kg/cm² or higher in reaction pressure,

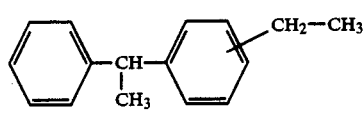
Formula (A)

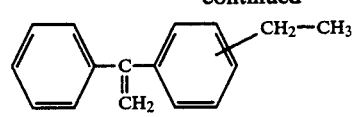
Formula (B)

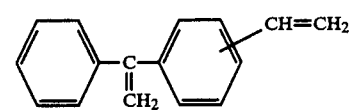
Formula (C)

The dehydrogenation catalyst used in the dehydrogenation step (I) is iron oxide catalyst, chromium oxide catalyst or a mixed catalyst of these oxides. This catalyst contains the main components of iron oxide, chromium oxide or the mixture of these oxides and suitable promoters of the oxide of molybdenum, vanadium, manganese, zinc, copper or the like. Furthermore, the oxide of alkali metal or alkaline earth metal such as sodium, potassium, magnesium, calcium or barium can be added in order to improve the efficiency of dehydrogenation. The form of these catalysts may be the one which is mainly composed of iron oxide or chromium oxide itself or carrier-supported catalyst which is supported on a carrier of, for example, alumina, silica-alumina or silica.

The dehydrogenation step (I) is carried out by diluting with an inert gas. This inert gas may be properly selected from those which do not inhibit the dehydrogenation reaction and which exert no inhibitive effect as catalyst poison. The inert gases are exemplified by inorganic gases such as nitrogen, hydrogen, helium, argon and steam and organic gas such as methane. Among them, steam is a preferable diluent in view of practical handling.

The dilution with an inert gas is preferably done with ten times by mole of an inert gas relative to the raw material of 1-phenyl-1-ethylphenyl-ethane. When the rate of dilution is too low, it is not desirable because the efficiency of dehydrogenation is low to reduce the reaction efficiency. In addition, the life of catalyst is shortened owing to the occurrence of coking. Even though the large ratio of the use of inert gas is effective, the upper limit of its molar ratio relative to 1-phenyl-1-ethylphenyl-ethane is practically about 500.

The quantity of feed of 1-phenyl-1-ethylphenylethane relative to the unit weight of catalyst is preferably 0.1 to 5 times by weight per hour. The feed quantity which is smaller than this range is not desirable because the starting material of 1-phenyl-1-ethylphenyl-ethane is decomposed and the demethylation in the portion of ethyl group connected to two aryl groups is caused to occur. Furthermore, when the feed quantity exceeds 5 times by weight, the reaction is not effective because the efficiency of dehydrogenation is too low.

The temperature of contact with the dehydrogenation catalyst is preferably in the range of 400° C. to 650° C. The range of 500° C. to 600° C. is more preferable. At temperatures below 400° C., the dehydrogenation efficiency is low and it is not practically acceptable. Meanwhile, at temperatures above 650° C., decomposition and demethylation of 1-phenyl-1-ethylphenyl-ethane itself become serious, which are not desirable.

The reaction pressure for the dehydrogenation is preferably a reduced pressure in view of the equilibrium in dehydrogenation and it is generally from a reduced pressure to about 5 kg/cm².

In the dehydrogenation step (I), 1-phenyl-1-ethylphenyl-ethane is dehydrogenated under the above conditions to convert it mainly into 1-phenyl-1-ethylphenyl-ethylene and 1-phenyl-1-vinylphenyl-ethylene. In other words, most part of the starting material of 1-phenyl-1-ethylphenylethane is converted into an internal olefin of 1-phenyl-1-ethylphenyl-ethylene of the formula (B) in which the ethane moiety having two aryl groups is converted into ethylene, and into a diolefin of 1-phenyl-1-vinylphenyl-ethylene of the formula (C) in which both the two ethane moieties in 1-phenyl-1-ethylphenyl-ethane are dehydrogenated. The dehydrogenation catalyst used in the present invention is a desirable catalyst because it excels in the efficiency of dehydrogenation of the starting material of the present invention. However, it cannot be avoided that at least two kinds of unsaturated hydrocarbon compounds of formulae (B) and (C) are produced as a mixture of them.

These unsaturated hydrocarbons are similar to each other in view of both the molecular weights and chemical structures. Therefore, their boiling points are close to each other, so that the efficient and economical separation of them is impossible by ordinary distillation. Furthermore, an external olefin of α-methylbenzylphenylethylene in which the ethyl group connected to one of the phenyl groups is converted into vinyl group, is also by-produced as a small amount of hydrogenation product. This is also hardly separated from the dehydrogenation product by an ordinary distillation operation. However, this external olefin does not cause substantially any disadvantage in the method of the present invention because the produced quantity of this is generally very small.

That is, under the condition in which 1-phenyl-1-vinylphenyl-ethylene is hydroformylated, the hydroformylation reaction does not give substantially any effect on the other olefin of 1-phenyl-1-ethylphenyl-ethylene.

Therefore, after the dehydrogenation step (I), the product can be passed as it stands to the next hydroformylation step (II) without subjecting it to any separation and refining treatment.

Furthermore, even though it depends upon the efficiency of dehydrogenation in the dehydrogenation step (I), the starting material of unreacted 1-phenyl-1-ethylphenylethane is also taken out. Without any separation, this can be also used intact for the next step (II) without any disadvantage.

Accordingly, the dehydrogenation product obtained from the foregoing step (I) is subjected to an ordinary industrial separation process, for example, separation by distillation, to recover a fraction containing at least 1-phenyl-1-ethylphenyl-ethylene and 1-phenyl-1-vinylphenylethylene and it is passed to the next step. Because the boiling points of 1-phenyl-1-ethylphenyl-ethylene and 1-phenyl-1-vinylphenyl-ethylene obtained in the step (I) are close to each other and the boiling point of the starting material of 1-phenyl-1-ethylphenyl-ethane is also close, the separation of them by means of industrial separation method such as ordinary distillation is difficult. Therefore, as far as the separation is done by industrial operation, it cannot be avoided that the fraction passed to the next step contains at least 1-phenyl-1-ethylphenyl-ethylene and 1-phenyl-1-vinylphenyl-ethylene together.

In other words, in the present invention, it is not necessary to separate the respective reaction products of the step (I) when they are passed to the step (II) from the step (I). It is practically impossible to separate the internal olefin of the formula (B), the diolefin of the formula (C) and the starting material of 1-phenyl-1-ethylphenyl-ethane of the formula (A) into the respective components. Even though it is not necessary that the dehydrogenation reaction product is refined, if desired, decomposition products and heavier polymeric substances which are by-produced in the step (I) can be separated. Therefore, the reaction product of the step (I) as a mixture can be fed to the next step (II) by subjecting it to a simple industrial operation of separation such as distillation. As the raw material for the step (II), a fraction in the boiling range of 80°-170° C., preferably 90°-160° C. at a reduced pressure of 2-3 mmHg, is used.

In the hydroformylation of the step (II), the materials of 1-phenyl-1-ethylphenyl-ethane of the formula (A) and 1-phenyl-1-ethylphenyl-ethylene of the formula (B) in the mixture obtained in the step (I) are not changed but 1-phenyl-1-vinylphenyl-ethylene of the formula (C) is changed into the aimed product of [(1-phenylethenyl)phenyl]propionaldehyde by hydroformylation. This aimed product of [(1-phenylethenyl)phenyl]propionaldehyde can be separated easily from the unreacted 1-phenyl-1-ethylphenyl-ethane of the formula (A) and 1-phenyl-1-ethylphenyl-ethylene of the formula (B), by an ordinary separation method such as distillation. Accordingly, it is possible to obtain the aimed product in high purity. In addition, 1-phenyl-1-ethylphenyl-ethane of the formula (A) and 1-phenyl-1-ethylphenyl-ethylene of the formula (B) which are separated from the mixture obtained in the step (II) can be used again as the starting materials for the step (I).

That is, the unreacted fraction obtained in the step (II) can be mixed with the starting material of 1-phenyl-1-ethylphenylethane of the formula (A) and fed to the dehydrogenation reaction of the step (I).

It is a matter of course that the unreacted 1-phenyl-1-ethylphenyl-ethane of the formula (A) in the step (II) can be used as a starting material for the step (I). From the unreacted 1-phenyl-1-ethylphenyl-ethylene of the formula (B), 1-phenyl-1-vinylphenyl-ethylene of the formula (C) is produced by the dehydrogenation in the foregoing step (II).

Furthermore, as the starting material of 1-phenyl-1-ethylphenyl-ethane in the foregoing dehydrogenation step (I), it is preferable that a fraction containing 1-phenyl-1-(3-ethylphenyl)ethane (hereinafter referred to as PEPE) is used, which fraction is recovered from a heavy fraction that is by-produced in the process of alkylation of benzene with ethylene in the presence of an alkylation catalyst. This material for dehydrogenation is described in the following.

In order to prepare a styrene monomer, a law material for producing polystyrene by dehydrogenation for producing polystyrene, it is widely carried out in industry to prepare ethylbenzene by alkylating benzene with ethylene.

In the preparation of ethylbenzene, benzene is firstly alkylated with ethylene in the presence of an alkylation catalyst to obtain an alkylation product mainly containing unreacted benzene, ethylbenzene, polyethylbenzene and heavier products. This can be done by known methods of ethylbenzene preparation such as liquid phase alkylation method and gas phase alkylation method. The molar ratio of benzene to ethylene can be about 25:1 to 2:1, preferably about 10:1 to 3:1. In the liquid phase reaction, the alkylation catalysts are exemplified by Friedel-Crafts catalysts such as aluminum chloride, aluminum bromide and other organic aluminum halides;

Lewis acids such as $ZnCl_2$, $FeCl_3$ and $BF_3$ containing a promoter; and Bronsted acids including sulfuric acid, sulfonic acid and p-toluenesulfonic acid. Benzene is reacted with ethylene in a temperature range of about 0°–175° C., preferably about 20°–150° C., in the presence of an alkylation catalyst described above of about 0.002–0.050 part by weight, preferably about 0.005–0.030 part by weight relative to ethylbenzene to be produced. When the reaction temperature is lower than 0° C., the yield of ethylbenzene is lowered. On the other hand, when the temperature is above 175° C., the yield of ethylbenzene is lowered due to side reaction, which is not desirable. With regard to the reaction pressure, a higher pressure is desirable in order to facilitate the dissolution of ethylene, however, the pressure up to 100 kg/cm$^2$ is practically employed. The duration of reaction is generally 10 minutes to 10 hours, preferably about 20 minutes to 3 hours.

In the gas phase alkylation method, the alkylation raw materials are brought into contact with an appropriate alkylation catalyst containing diatomaceous earth, silica or alumina, or aluminum silicate carrying phosphoric acid, or synthetic zeolite catalyst such as ZSM-5 type synthetic zeolite, at a temperature in the range of about 250°–450° C., preferably about 300°–400° C., and a pressure in the range of about 28–85 kg/cm$^2$, preferably about 42–70 kg/cm$^2$, at an ordinary space velocity.

As a result of the alkylation, alkylation products of unreacted benzene, aimed ethylbenzene, polyethylbenzene and heavier product containing PEPE are obtained. If desired, the contained alkylation catalyst is removed from the alkylation products. For example, when aluminum chloride is used as an alkylation catalyst, the alkylation products are fed to a settler, in which the aluminum chloride is precipitated and removed. If necessary, the removed catalyst is recycled to the reaction system. The remaining alkylation products are then rinsed with water and neutralized.

Then, a fraction containing PEPE (hereinafter referred to as dehydrogenation raw material fraction of the present invention) is recovered from the above alkylation products mainly containing unreacted benzene, ethylbenzene, polyethylbenzene and heavier product containing PEPE.

In this recovery process, the alkylation products is distilled under atmospheric pressure or a reduced pressure to obtain a heavier products by distilling off the unreacted benzene (boiling point 80° C.), ethylbenzene (boiling point 136° C.) and polyethylbenzene (boiling point 176°–250° C.), respectively. The raw material fraction of the present invention can be obtained by distilling further the heavier product. While, the raw material fraction of the present invention can be obtained by directly distilling the alkylation products. Either method will do.

The boiling point of the raw material fraction of the present invention which is recovered by the above method must be in the range of 275°–305° C., preferably 285°–300° C. When the boiling point is above 305° C., the fraction contains PEPE as well as much 1,1-(4-ethylphenyl)phenylethane, which is a p-isomer of PEPE. If this 1,1-(4-ethylphenyl)phenylethane is treated in a succeeding step, the derivative from this compound is hardly separated. Accordingly, it is desirable that the boiling point of the raw material fraction of the present invention does not exceed 305° C. In the case that the boiling point is lower than 275° C., it is not desirable in that the treatment in the succeeding process is uneconomical because the content of PEPE is lowered.

In the raw material fraction of the present invention, PEPE is contained in a high concentration, while the o-isomer of 1,1-(2-ethylphenyl)phenylethane is not contained substantially. However, besides PEPE, several impurities typically exemplified by polyalkylbenzenes including various isomers are contained in this fraction. With regard to these polyalkylbenzenes, accurate structural analysis is difficult and the boiling points of them are close to that of PEPE, therefore, the refining of PEPE by means of any ordinary method is difficult. This is the reason why the effective use of PEPE in such a fraction has never been accomplished.

The dehydrogenation raw material fraction of the present invention which is prepared by the above described process is used for the foregoing dehydrogenation step (I) and then it is hydroformylated in the hydroformylation step (II).

$\alpha$-[m-(1-Phenylethenyl)phenyl]propionaldehyde, that is the m-isomer of [(1-phenylethenyl)phenyl]propionaldehyde obtained through the method of the present invention, is easily converted into a medicine of Ketoprofen (trade name) by oxidizing it by a conventional oxidation methods such as permanganate oxidation, hypochlorite oxidation, or oxidation by contact with molecular oxygen in the presence of an oxidation catalyst.

According to the present invention, the diolefin having a vinyl group of (1-arylethenyl)vinylbenzene of the formula (I) is selectively hydroformylated. That is, only the vinyl group is hydroformylated to produce $\alpha$-((1-arylethenyl)phenyl)propionaldehyde of the foregoing formula (II).

In addition, in the present invention, the reaction product obtained from the dehydrogenation step of (I) is treated only by the industrial distillation operation and it is then fed to the next hydroformylation step (II) without any refining treatment. Even when such a mixture is hydroformylated, the aimed product in quite a high purity can be obtained.

In general, it cannot be considered to utilize a reaction without refining treatment which oncludes side reaction to produce resembling compounds. However, this was made possible for the above described reason in the present invention.

Accordingly, the method of the present invention is economical and valuable in view of industry as it is possible to exert sufficiently a high efficiency of the dehydrogenation catalyst.

BEST MODE FOR CARRYING OUT THE INVENTION

The present invention is described in the following with reference to examples.

REFERENCE EXAMPLE 1

Synthesis of 1-(3-vinylphenyl)-1-phenylethylene

To a 2 liter three-neck flask equipped with a dropping funnel, a reflux condenser and a stirrer was added 25.5 g (1.05 mole) of metallic magnesium and it was dried sufficiently by supplying dry nitrogen gas. After that, 50 ml of tetrahydrofuran which had been dried with a molecular sieve 5A, was put into the flask and the contents were stirred vigorously. A solution of 183 g (1.0 mole) of 3-vinylbenzene bromide in 500 ml of dried tetrahydrofuran was then dropped little by little over 2 hours. The reaction temperature was maintained 75° to 80° C. and, after the addition of the solution, the stirring was continued for further 1 hour as it stands. Into the thus obtained Grignard reagent of 3-vinylphenylmagnesium bromide, a solution of 122.6 g (1.02 mole) of acetophenone in 500 ml of dried tetrahydrofuran was dropped little by little over 2 hours. The reaction temperature was maintained at 75° to 80° C. and, after the dropping, the stirring was continued for further 1 hour as it stands. The reaction mixture was then poured into 3 liter of an aqueous solution of 75 g of ammonium chloride and it was left to stand still for 20 hours and an oily layer was recovered to obtain 1-(3-vinylphenyl)-1-phenylethyl alcohol in a yield of 89% (acetophenone basis) by distilling off the tetrahydrofuran.

To a 300 ml three-neck flask with a distillation column and a dropping funnel was added 81 g of potassium hydrogensulfate and the pressure was reduced to 15 to 20 mmHg. The obtained alcohol was then dropped into the flask little by little over 2 hours. The water produced by dehydration and oily components were recovered from the top of the distillation column and 1-(3-vinylphenyl)-1-phenylethylene was obtained in a yield of 100% (on the basis of raw material alcohol) from the oily layer by a separatory funnel. The dehydration reaction was carried out at a temperature of 200° to 250° C. The analytical data on the thus produced 1-(3-vinylphenyl)-1-phenylethylene (formula I) are shown in the following:

Boiling Point: 134.0°-135.5° C./2.0-3.0 mmHg

IR: (Neat) cm$^{-1}$ 3050, 1690, 1495, 1260, 995, 900, 810, 780, 700

$^1$H-NMR: (CCl$_4$, δppm) 7.10-7.70, (9H Multiplet) 6.65-6.80, (1H Quadruplet) 5.65-5.80, (1H Doublet) 5.45-5.50, (2H Doublet) 5.20-5.30, (1H Doublet)

Elemental Analysis: (as C$_{16}$H$_{14}$)
Calculated: C: 93.20%
Found: H: 6.80%, C: 93.24%, H: 6.76%

EXAMPLE 1

Preparation of α-(3-(1-phenylethenyl)phenyl)propionaldehyde

To a 500 ml autoclave with a stirrer were added 50 g of 1-(3-vinylphenyl)-1-phenylethylene obtained in Reference Example 1 and 0.6 g of rhodium hydridocarbonyl tristriphenylphosphine. The pressure was raised up to 60 kg/cm$^2$ by a mixed gas of hydrogen and carbon monoxide (molar ratio 1:1) and reaction was continued until the absorption of the mixed gases caused by the reaction was ceased. The reaction temperature was 60° C. After the reaction, the temperature was lowered to room temperature and unreacted mixed gases were removed to recover the reaction product. This was subjected to reduced pressure distillation to obtain α-(3-(1-phenylethenyl)propionaldehyde in a yield of 73% at a distilling temperature of 125.5°-126.5° C./0.5-1 mmHg. As a result of GC analysis, it was found that the α-(3-(1-phenylethenyl)phenyl)propionaldehyde was 96%. Furthermore, the compound of internal olefin in which the ethylidene type double bond was hydroformylated was not substantially observed. The results of spectrum analysis of α-(3-(1-phenylethenyl)phenyl)propionaldehyde are shown in the following.

IR: (Neat) cm$^{-1}$ 3055, 2995, 2850, 2730, 1740, 1620, 1500, 1445, 1380, 1060, 900, 750, 700

$^1$H-NMR: (CCl$_4$, δppm), 9.80, (1H Singlet), 6.90-7.45 (9H Multiplet), 3.05-3.55 (1H Quadruplet), 5.09 (2H Singlet), 1.30-1.47 (3H Doublet), Elemental Analysis: (as C$_{17}$H$_{16}$O)
Calculated: C: 86.44%, H: 6.78%, O: 6.78%
Found: C: 86.50%, H: 6.80%, O: 6.70%

EXAMPLE 2

Step (I) Dehydrogenation of 1-phenyl-1-ethylphenyl-ethane

An iron oxide dehydrogenation catalyst of G-64C (trade mark) made by Nissan Girdler Catalysts Co., Ltd. of 15 to 25 mesh in particle diameter was used. To a reaction tube of 560° C. were fed continuously 10 ml/hr of a fraction of 1-phenyl-1-ethylphenyl-ethane having a boiling range of 285° C. to 305° C. (at atmospheric pressure) and 100 ml/hr of water and the outlet of the reaction tube was cooled. The oily layer obtained after separation and settling was analyzed by gas chromatography. The analytical results on the oily layer which was obtained from 4 hours to 76 hours after the start of reaction are shown in the following.

TABLE 1

| Components | Results of Analysis Anaytical Value (%) |
|---|---|
| Light Fraction | 2.7 |
| 1,1-Diphenylethane | 0.6 |
| 1-m-Ethylphenyl-1-phenylethane | 19.0 |
| 1-m-Vinylphenyl-1-phenylethane | 2.1 |
| 1-m-Ethylphenyl-1-phenylethylene | 32.9 |
| 1-m-Vinylphenyl-1-phenylethylene | 41.1 |
| Heavy Fraction | 1.6 |
| Total | 100.0 |

EXAMPLE 3

Dehydrogenation of 1-phenyl-1-ethylphenyl-ethane was carried out in the like manner as in Example 1 except that a chromium oxide/iron oxide dehydrogenation catalyst of G-64A (trade mark) made by Nissan Girdler Catalysts Co., Ltd. was used.

Oily layer was recovered from 4 hours to 12 hours after the start of reaction. The results of gas chromatographic analysis of this material are shown in the following.

TABLE 2

| Components | Results of Analysis Analytical Value (%) |
|---|---|
| Light Fraction | 3.1 |
| 1,1-Diphenylethane | 0.8 |
| 1-m-Ethylphenyl-1-phenylethane | 23.6 |
| 1-m-Vinylphenyl-1-phenylethane | 1.3 |
| 1-m-Ethylphenyl-1-phenylethylene | 37.1 |
| 1-m-Vinylphenyl-1-phenylethylene | 32.2 |
| Heavy Fraction | 1.9 |
| Total | 100.0 |

EXAMPLE 4

Dehydrogenation of 1-phenyl-1-ethylphenyl-ethane was carried out in the like manner as in Example 2 except the conditions shown in the following Table 3.

The results of tests are shown also in Table 3.

TABLE 3

| Number | 4a | 4b | 4c | 4d | 4e |
| --- | --- | --- | --- | --- | --- |
| 1-m-Ethylphenyl-1-phenylethane (ml/h) | 10 | 20 | 40 | 10 | 10 |
| Diluent | Nitrogen | Water | Water | Water | Water |
| Do., Feed Qty. (ml/hr) | 2000 | 200 | 200 | 100 | 100 |
| Reaction Temper. (°C.) | 560 | 600 | 600 | 450 | 500 |
| Analytical Results (%) | | | | | |
| Light Fraction | 3.4 | 4.4 | 1.9 | 0.8 | 1.4 |
| 1,1-Diphenylethane | 0.6 | 0.7 | 0.2 | 0.1 | 0.4 |
| 1-m-Ethylphenyl-1-phenylethane | 20.6 | 25.7 | 30.6 | 73.9 | 58.5 |
| 1-m-Vinylphenyl-1-phenylethane | 1.6 | 1.8 | 1.7 | 1.2 | 1.4 |
| 1-m-Ethylphenyl-1-phenylethylene | 33.3 | 33.4 | 39.4 | 15.6 | 27.8 |
| 1-m-Vinylphenyl-1-phenylethylene | 37.7 | 30.3 | 23.8 | 7.8 | 9.4 |
| Heavy Fraction | 2.8 | 3.7 | 2.4 | 0.6 | 1.1 |

EXAMPLE 5

Step (II) Hydroformylation

The reaction product obtained in Example 2 was distilled at a reduced pressure of 2 mmHg to 3 mmHg by an ordinary distillation apparatus to obtain a dehydrogenation product of a fraction having a distilling temperature of 100° C. to 150° C. (recovery rate 94%). This was subjected to hydroformylation.

To a 500 ml autoclave with a stirrer were added 100 g of the above fraction, 100 mg of rhodium hydridocarbonyl tristriphenylphosphine and 60 mg of triphenylphosphine. The pressure was maintained at 90 kg/cm$^2$ by a mixed gas of carbon monoxide and hydrogen of 1:1 in molar ratio and the reaction was continued for 12 hours at 110° C. After the reaction, the reaction mixture was cooled and unreacted gas was discharged. Then, 51.5 g of a fraction (a) of a distilling temperature of 105° C. to 115° C. at a reduced pressure of 0.5 mmHg to 1 mmHg and 38.3 g of a fraction (b) of a distilling temperature of 120° C. to 130° C. were obtained by the reduced pressure distillation.

The composition of the fraction (a) was 35.9% of 1-m-ethylphenyl-1-phenylethane and 63.6% of 1-m-ethylphenyl-1-phenylethylene. It could be confirmed that the dehydrogenation product of the step (I) of 1-phenyl-1-ethylphenylethylene did not reacted in the hydroformylation of the step (II).

The composition of the fraction (b) was [m-(1-phenylethenyl)phenyl]propionaldehyde of 94.4% in purity and the ratio in α-aryl compound/β-aryl compound was 8.9. Furthermore, in [m-(1-phenylethenyl)-phenyl]propionaldehyde, the double bond in the ethylene moiety having two phenyl groups was maintained and only the ethylene moiety having one phenyl group was hydroformylated.

EXAMPLE 6

The reaction product obtained in the step (I) was hydroformylated in the like manner as Example 5 except that 85 mg of iridium hydridocarbonyl tristriphenylphosphine and 60 mg of triphenylphosphine were used as hydroformylation catalysts.

The composition and recovery rate of fraction (a) obtained by reduced pressure distillation were the same as those in Example 5. Furthermore, the fraction (b) was [m-(1-phenylethenyl)phenyl]propionaldehyde of 93.7% in purity and the ratio in α-aryl compound/β-aryl compound was 6.3, and only the ethylene moiety having one phenyl group was hydroformylated.

Reference Example

Preparation of Ketoprofen by Oxidation of Aldehyde

The fraction (b) obtained in Example 5 was subjected to precision fractional distillation to obtain α-[m-(1-phenylethenyl)phenyl]propionaldehyde of 123° C. to 128° C. in distilling temperature at a reduced pressure of 0.5 mmHg to 1 mmHg (purity 98.5% and ratio in α-aryl comp./β-aryl comp. 51.5).

To a 300 ml autoclave with a stirrer were fed 15 g of the obtained propionaldehyde, 0.03 g of cobalt naphthenate and 100 ml of decane as a solvent. The pressure was maintained at 10 kg/cm$^2$ at a temperature of 70° C. by pure oxygen and it was allowed to react for 16 hours.

After the reaction, the solvent was removed by reduced-pressure distillation to obtain a solid substance, which was washed five times with 500 ml of water and it was dissolved in 500 ml of ether and washed with water further three times. After that, the ether was removed by reduced-pressure distillation and the obtained product was recrystallized with a benzene/petroleum ether mixture to obtain 10 g of α-(3-benzoylphenyl)propionic acid (trade name: ketoprofen). The melting point and the spectrum of the product were the same as those of an authentic sample.

With regard to the propionaldehyde in Example 6, it was confirmed that, by oxidizing likewise, ketoprofen which was the same as the authentic sample could be obtained.

EXAMPLE 7

Benzene and ethylene in a molar ratio of 9:1 were allowed to contact together for 1 hour in liquid phase with stirring in a reaction vessel at a temperature of 130° C. and a pressure of 4.9 kg/cm$^2$ in the presence of aluminum chloride. The duration of 1 hour was sufficient for adding the whole ethylene. The use quantity of aluminum chloride was 0.0034 part by weight relative to the produced ethylbenzene. As a result of the analysis of the obtained alkylation product, it was understood that 49.0% by weight of benzene, 32.9% by weight of ethylbenzene, 17.5% by weight of polyethylbenzene and 0.5% by weight of heavier product were contained. Unreacted benzene, ethylbenzene and polyethylbenzene were recovered by distilling this alkylation product to obtain the heavier product which was 0.014 part by weight relative to the produced ethylbenzene. This heavier product was further subjected to distillation to obtain a fraction of a boiling range of 280°–305° C. (as atmospheric pressure). As a result of analysis of this product, it was found out that it was 82% of PEPE and 18% of impurity mainly containing polyalkylbenzene.

The obtained fraction (124 g) was then subjected to dehydrogenation and hydroformylation according to Example 2 and Example 5.

As a result, α-(m-(1-phenylethenyl)phenyl)-propionaldehyde as a fraction of distilling temperature of 120° C.–130° C. at 0.5–1 mmHg in a yield of 31% was obtained (purity 94.4%, ratio in α-aryl comp./β-aryl comp. 8.9).

With regard to this material, it was confirmed that, by oxidizing like the foregoing Reference Example 2, ketoprofen which was the same as the authentic sample could be obtained.

We claim:

1. A process for selective hydroformylation which is characterized in the step of reacting a (1-arylethenyl)-vinylbenzene represented by the following formula (I) with carbon monoxide and hydrogen at a reaction temperature ranging from 40° to 200° C. and at a reaction pressure ranging from 5 kg/cm² to 500 kg/cm² in the presence of a transition metal carbonylation catalyst, thereby producing α-((1-arylethenyl)-phenyl)propionaldehyde represented by the following formula (II), wherein Ar is an aryl group selected from the group consisting of phenyl group, biphenyl group and naphthyl group, which is unsubstituted or substituted with at least one substituent selected from the group consisting of alkyl group, hydroxyl group, alkoxy group, phenoxy group, carboxyl group, and alkoxycarbonyl group,

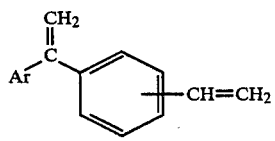

Formula (I)

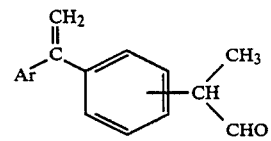

Formula (II)

2. The process for selective hydroformylation in claim 1, wherein 3-(1-phenylethenyl)vinylbenzene is reacted with carbon monoxide and hydrogen in the presence of a transition metal complex carbonylation catalyst, thereby producing α-(3-(1-phenylethenyl)-phenyl)propionaldehyde.

3. The process in claim 1 wherein 1,1-di(substituted aryl) ethylenes represented by the following formula III

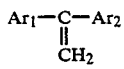

(III)

are additionally present, in which
Ar₁ and Ar₂ are the same or different and are an aryl group selected from the group consisting of phenyl group, biphenyl group, and naphthyl group, which is unsubstituted or substituted with at least one substituent selected from the group consisting of alkyl group, hydroxy group, alkoxy group, phenoxy group, carboxyl group and alkoxy-carbonyl group.

4. The process in claim 3, wherein said 1,1-di(substituted aryl)ethylene of the formula (III) is 1-phenyl-1-ethylphenylethylene.

5. The process in claim 3, wherein ((1-phenylethenyl)phenyl)propionaldehyde is produced by the following step (I) and step (II).

Step (I): 1-phenyl-1-ethylphenyl-ethane represented by the formula (A) is brought into contact with iron oxide and/or chromium oxide dehydrogenation catalyst at a temperature of 400° C. to 650° C. in the presence of an inert gas to obtain a dehydrogenation product containing at least 1-phenyl-1-ethylphenyl-ethylene represented by the formula (B) and 1-phenyl-1-vinylphenyl-ethylene represented by the formula (C), and Step (II): the dehydrogenation product obtained in the Step (I) containing at least 1-phenyl-1-ethylphenyl-ethylene represented by the formula (B) and 1-phenyl-1-vinylphenylethylene represented by the formula (C) is hydroformylated with carbon monoxide and hydrogen in the presence of a transition metal carbonylation catalyst, at a reaction temperature of 40°–200° C. and a reaction pressure of 5 kg/cm² to 500 kg/cm².

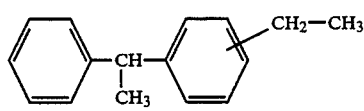

Formula (A)

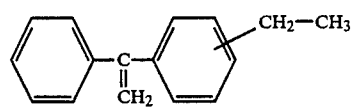

Formula (B)

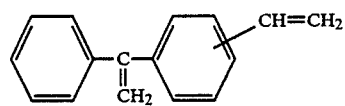

Formula (C)

6. The process in claim 5, wherein said dehydrogenation catalyst contains iron oxide and/or chromium oxide.

7. The process in claim 5, wherein a fraction containing highly pure ((1-phenylethenyl)phenyl)propionaldehyde is recovered by distillation after said hydroformylation step.

8. The process in claim 5, wherein, after said hydroformylation step, unreacted 1-phenyl-1-ethylphenylethane and/or 1-phenyl-1-ethylphenyl-ethylene is recovered by separation and it is then returned to said dehydrogenation step (I).

9. The process in claim 5, wherein said 1-phenyl-1-ethylphenyl-ethane is a fraction which contains 1-phenyl-1-ethylphenyl-ethane and which is recovered from the heavy by-product fraction in the preparation of ethylbenzene by alkylating benzene with ethylene.

10. The process in claim 9, wherein the catalyst used for alkylation is aluminum chloride or synthetic zeolite catalyst.

11. The process in any one of claims 1 to 10, wherein the transition metal carbonylation catalyst contains at least one metal as active component selected from the group consisting of Pt, Rh, Ir, Ru, Co and Ni.

12. The process according to claim 1 wherein the alkyl group and alkoxy groups contain from 1–4 carbon atoms.

13. The process according to claim 1 wherein Ar is phenyl or biphenyl.

14. The process according to claim 13 wherein the alkyl groups and alkoxy groups contain 1–2 carbon atoms.

15. The process according to claim 3 wherein the alkyl and alkoxy groups contain from 1–4 carbon atoms.

* * * * *

UNITED STATES PATENT AND TRADEMARK OFFICE
CERTIFICATE OF CORRECTION

PATENT NO. : 4,982,007

DATED : January 1, 1991

INVENTOR(S) : Isoo Shimizu, et al.

It is certified that error appears in the above-identified patent and that said Letters Patent is hereby corrected as shown below:

On the Title page, Section [54]: "HYDROFORMULATING" should read as --HYDROFORMYLATING--

On the Title page, Section [62]: "Division" should read as --Continuation--

In the Abstract, line 2: "(1-arylethyl)" should read as --(1-arylethenyl)--

Column 1, line 2: "HYDROFORMULATING" should read as --HYDROFORMYLATING--

Signed and Sealed this

Thirtieth Day of June, 1992

*Attest:*

DOUGLAS B. COMER

*Attesting Officer*  *Acting Commissioner of Patents and Trademarks*